US00PP22798P2

(12) United States Plant Patent
Smith

(10) Patent No.: US PP22,798 P2
(45) Date of Patent: Jun. 19, 2012

(54) ***CHRYSANTHEMUM* PLANT NAMED 'SYCASS BRON'**

(50) Latin Name: *Chrysanthemum×morifolium*
Varietal Denomination: Sycass Bron

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/065,149

(22) Filed: Mar. 15, 2011

(51) Int. Cl.
*A01H 5/00* (2006.01)

(52) U.S. Cl. ..... Plt./296

(58) Field of Classification Search ..... Plt./296, Plt./290

See application file for complete search history.

*Primary Examiner* — Annette Para
(74) *Attorney, Agent, or Firm* — Joshua L. Price

(57) ABSTRACT

A new *Chrysanthemum* plant named 'Sycass Bron' particularly distinguished by the greyed-orange colored inflorescences, medium green foliage, good mounding habit and a natural flowering season of mid September.

1 Drawing Sheet

Latin name of the genus and species of the plant claimed: *Chrysanthemum×morifolium.*

Varietal denomination: 'Sycass Bron'.

BACKGROUND OF THE NEW PLANT

The present invention comprises a new *Chrysanthemum*, botanically known as *Chrysanthemum×morifolium*, and hereinafter referred to by the variety name 'Sycass Bron'.

'Sycass Bron' is a product of a planned breeding program. The new cultivar has greyed-orange colored inflorescences, medium green foliage, good mounding habit and a natural flowering season of mid-September.

'Sycass Bron' originated from a hybridization made in October 2005 in a controlled breeding environment in Tenjo, Columbia. The female parent was an unknown variety, as several small seed lots were bulked together when that generation was sown.

The male parent of 'Sycass Bron' was identified as 'Cyclops', an unpatented variety with a smaller and darker flower color, more disc florets, a more spreading plant habit and a natural flowering season that is 5-7 days slower. The resultant seed was sown in June 2005 in Alva Fla.

'Sycass Bron' was selected as one flowering plant within the progeny of the stated cross in the November 2005 in a controlled environment in Alva, Fla.

The first act of asexual reproduction of 'Sycass Bron' was accomplished when vegetative cuttings were propagated from the initial selection in December 2005 in a controlled environment in Alva, Fla.

BRIEF SUMMARY OF INVENTION

Horticultural examination of plants grown from cuttings of the plant initiated in December 2005 and continuing thereafter, has demonstrated that the combination of characteristics as herein disclosed for 'Sycass Bron' are firmly fixed and are retained through successive generations of asexual reproduction.

'Sycass Bron' has not been observed under all possible environmental conditions. The phenotype may vary significantly with variations in environment such as temperature, light intensity and day length.

A Plant Breeder's Right for this cultivar has been applied for in Canada on March 19, 2010 (No. 10-6890). 'Sycass Bron' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Sycass Bron' with colors being as true as possible with an illustration of this type.

Figure 1:
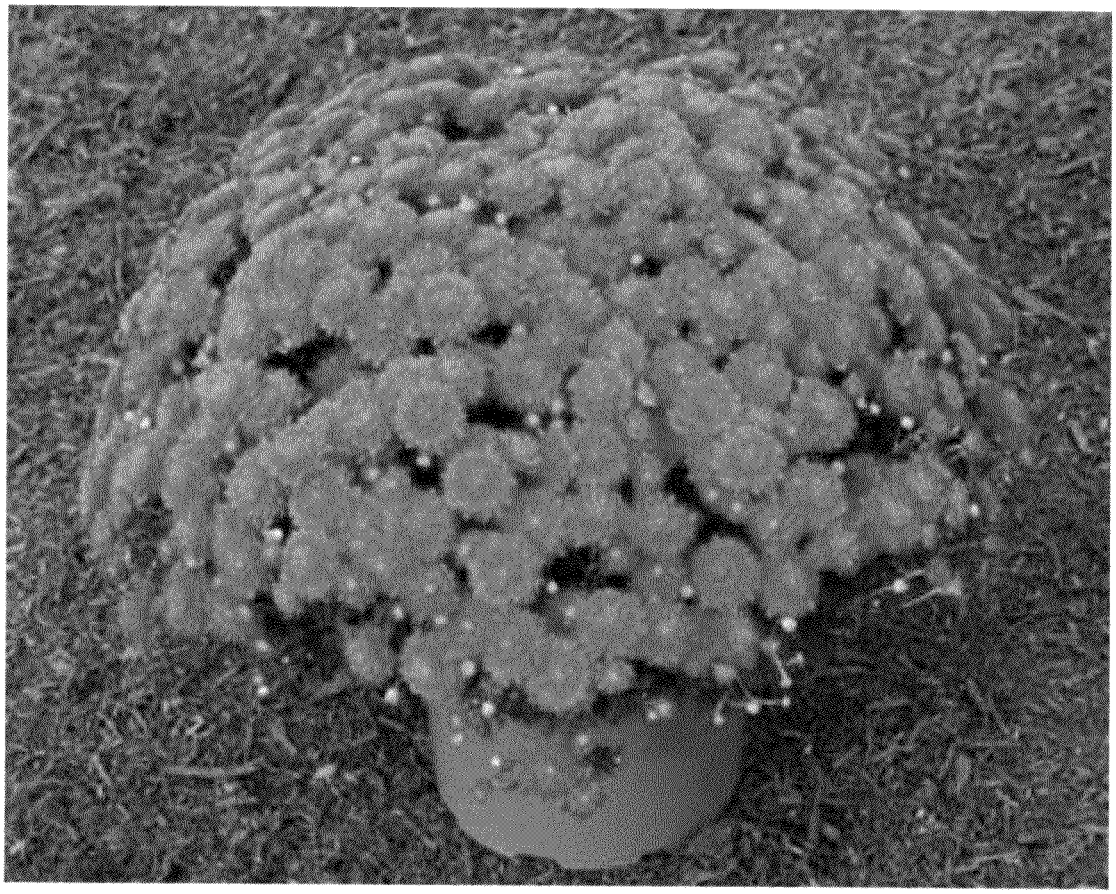
Figure 2:
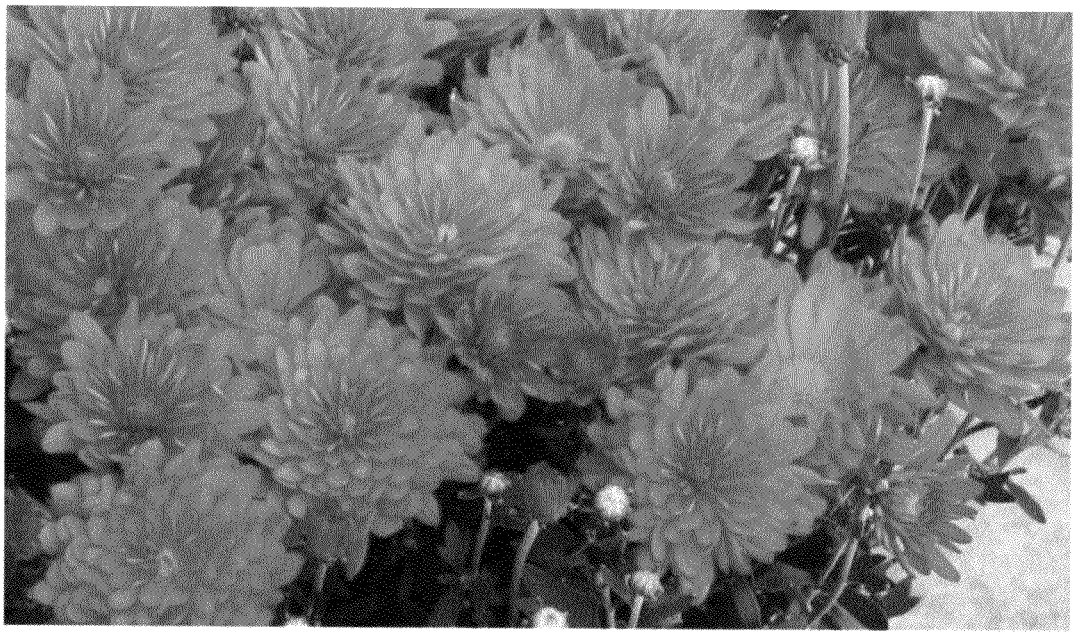

The photographic drawing shows in FIG. 1 a flowering potted plant of the new variety, in FIG. 2 a close-up of the flowers.

DETAILED BOTANICAL DESCRIPTION

The plant used for the photographs was about 14 weeks old grown in Monroeville, N.J. in an outdoor trial. One rooted cuttings grown in a nine inch pot with no terminal pinching of the apices. The photograph was taken in mid September 2010 in New Jersey.

The plant descriptions and measurements were taken from plants that were growing in an outdoor trial in Gilroy, Calif. The plants were grown in 1 gallon pots and were about 10-12 weeks old.

Color references are made to The Royal Horticultural Society Colour Chart (R.H.S.) 2001.

TABLE 1

DIFFERENCES BETWEEN THE NEW VARIETY 'SYCASS BRON' AND A SIMILAR VARIETY

| | 'Sycass Bron' | 'Flashy Yogretchen' (U.S. Plant Pat. No. 17,846) |
|---|---|---|
| Flower size: | Somewhat larger | Somewhat smaller |
| Plant size: | Somewhat smaller | Somewhat larger |
| Natural flowering season response: | 1 week faster | 1 week slower |

Plant:
*Form, growth and habit*.—Herbaceous decorative garden-type, stems upright and outwardly spreading, freely branching, strong and moderately vigorous growth habit.
*Plant height*.—Approximately 20 cm.
*Plant height* (*inflorescence included*).—Approximately 28 cm.
*Plant width*.—Approximately 40 cm.
*Garden performance and tolerance to weather*.—Very good.

Roots:
*Number of days to initiate roots*.—4 days at about 22 degrees C.
*Number of days to produce a rooted cutting*.—10-12 days at 22 degrees C.
*Type*.—Fine, fibrous, free branching.
*Color*.—RHS N155B but whiter.

Foliage:
*Arrangement*.—Alternate.
*Immature, leaf color, upper surface*.—Between RHS 137A and RHS 137B.
*Lower surface*.—RHS 137C.
*Mature, leaf color, upper surface*.—RHS 137A.
*Lower surface*.—Between RHS 137B and RHS 137C.
*Length*.—4.4-4.6 cm.
*Width*.—2.7-4.1 cm.
*Shape*.—Ovate to broadly ovate.
*Base shape*.—Attenuate.
*Apex shape*.—Mucronulate.
*Margin*.—Irregularly lobed, palmately incised and serrate.
*Texture, upper surface*.—Bifid T-shaped hairs.
*Lower surface*.—Bifid T-shaped hairs.
*Color of veins, upper surface*.—RHS 146C.
*Color of veins, lower surface*.—RHS 146C.
*Petiole color*.—RHS 146C.
*Length*.—1.1-2.1 cm.
*Diameter*.—0.2 cm.
*Texture*.—Bifid T-shaped hairs.

Stem:
*Quantity of main branches per plant*.—About 6 with many secondary branches.
*Color of stem*.—RHS 138A but appears lighter with the hairs.
*Length of stem*.—13-15 cm.
*Diameter*.—0.3-0.4 cm.
*Length of internodes*.—1.2-3.5 cm.
*Texture*.—Bifid T-shaped hairs.
*Color of peduncle*.—RHS 138A.
*Length of peduncle*.—7.5-12.0 cm.
*Peduncle diameter*.—0.15-0.2 cm.
*Texture*.—Bifid T-shaped hairs.

Inflorescence:
*Type*.—Compositae type, solitary decorative-type inflorescences, borne terminally above foliage, ray florets arranged acropetally on a capitulum.
*Quantity of short days to flowering* (*response time*).—About 47 days.
*Natural season flowering*.—Mid-September.
*Quantity of inflorescences per plant*.—110-120 plus numerous buds.
*Lastingness of individual blooms on the plant*.—About 6 weeks from first flower.
*Fragrance*.—Lightly spicy.

Bud (just when opening/showing color):
*Color*.—RHS 178A.
*Length*.—1.3-1.4 cm.
*Width*.—1.0-1.1 cm.
*Shape*.—Oblate.

Immature inflorescence:
*Diameter*.—3.5-4.0 cm.
*Color of ray florets, upper surface*.—Closest to RHS 179A and slightly mottled.
*Lower surface*.—RHS 14D overlaid with RHS 171A.

Mature inflorescence:
*Diameter*.—4.5 cm.
*Depth*.—2.0 cm.
*Total diameter of 'disc'*.—0.6-0.7 cm.
*Receptacle height*.—0.3 cm.
*Receptacle diameter*.—0.4-0.5 cm.

Ray florets:
*Average quantity of florets*.—Approximately 150 in numerous whorls.
*Color of florets, upper surface*.—RHS 171A to RHS 171B with RHS N170B mottled in.
*Lower surface*.—RHS 162C base, heavy overlay RHS 166B in varying hues.
*Length*.—2.4-2.5 cm.
*Width*.—0.6 cm.
*Shape*.—Narrowly elliptical or oblong.
*Apex shape*.—Praemorse.
*Margin*.—Entire.
*Texture, upper surface*.—Papillose.
*Lower surface*.—Papillose.

Disc florets:
*Average quantity of florets*.—20-25.
*Color of florets*.—RHS 155C basally with RHS 9A apex.
*Length*.—0.3 cm.
*Width*.—0.1 cm.
*Shape*.—Tubular, elongated.
*Apex shape*.—Acute, 5 pointed.

Phyllaries:
*Quantity*.—Approximately 25-30.
*Color, upper surface*.—RHS 146A but a little darker.
*Lower surface*.—RHS 146A.
*Length*.—0.5 cm.
*Width*.—0.15-0.2 cm.
*Shape*.—Ovate.
*Apex shape*.—Acute.
*Based*.—Fused.
*Margins*.—Entire, with some papery margins.
*Texture, upper surface*.—Glabrous.
*Lower surface*.—Bifid T-shaped hairs.

Reproductive organs:
*Pistil*.—1.
*Length*.—0.3-0.4 cm.
*Style color*.—About RHS 1B.
*Style length*.—0.3-0.4 cm.
*Stigma color*.—RHS 1C.
*Stigma shape*.—Bi-parted.
*Ovary color*.—Not observed.
*Stamens*.—1.
*Color of filaments*.—RHS 1C.
*Length filaments*.—0.3 cm.
*Anther color*.—RHS 3D.
*Anther length*.—0.1 cm.
*Anther shape*.—Oval.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Sycass Bron' substantially as illustrated and described herein.

* * * * *